US009113890B2

(12) United States Patent
Dasnurkar et al.

(10) Patent No.: US 9,113,890 B2
(45) Date of Patent: Aug. 25, 2015

(54) DEVICES AND METHODS FOR OCCLUDING VASCULAR ABNORMALITIES

(75) Inventors: Anup Dasnurkar, Maple Grove, MN (US); Jana Santer, Spring Lake Park, MN (US); Matthew C. Heidner, Maple Grove, MN (US)

(73) Assignee: AGA MEDICAL CORPORATION, Plymouth, MN (US)

( * ) Notice: Subject to any disclaimer, the term of this patent is extended or adjusted under 35 U.S.C. 154(b) by 321 days.

(21) Appl. No.: 13/367,011

(22) Filed: Feb. 6, 2012

(65) Prior Publication Data
US 2013/0204289 A1    Aug. 8, 2013

(51) Int. Cl.
 A61M 29/00    (2006.01)
 A61B 17/12    (2006.01)
 A61B 17/00    (2006.01)

(52) U.S. Cl.
 CPC ..... *A61B 17/12113* (2013.01); *A61B 17/12172* (2013.01); *A61B 17/12177* (2013.01); *A61B 2017/00526* (2013.01); *A61B 2017/00592* (2013.01); *A61B 2017/00862* (2013.01); *A61B 2017/00867* (2013.01)

(58) Field of Classification Search
 CPC ................. A61B 17/12113; A61B 17/121172; A61B 17/12177; A61B 2017/00592; A61B 2017/00867; A61B 2017/00862
 USPC ................. 606/200, 213, 151; 623/1.11, 1.35, 623/1.15, 1.2
 See application file for complete search history.

(56) References Cited

U.S. PATENT DOCUMENTS

| | | | |
|---|---|---|---|
| 5,645,558 | A | 7/1997 | Horton |
| 5,911,731 | A | 6/1999 | Pham et al. |
| 6,168,622 | B1 | 1/2001 | Mazzocchi |
| 6,391,037 | B1 | 5/2002 | Greenhalgh |
| 6,632,241 | B1 | 10/2003 | Hancock et al. |
| 8,034,061 | B2 | 10/2011 | Amplatz et al. |
| 2001/0012949 | A1 | 8/2001 | Forber |
| 2006/0247680 | A1 | 11/2006 | Amplatz et al. |
| 2007/0265656 | A1 | 11/2007 | Amplatz et al. |
| 2008/0200945 | A1 | 8/2008 | Amplatz et al. |

(Continued)

FOREIGN PATENT DOCUMENTS

WO    WO 2009/132045 A2    10/2009

OTHER PUBLICATIONS

International Search Report and Written Opinion for Application No. PCT/US2013/024608, dated Jul. 15, 2013.

*Primary Examiner* — Thomas McEvoy
*Assistant Examiner* — Julie A Szpira
(74) *Attorney, Agent, or Firm* — Armstrong Teasdale LLP

(57) ABSTRACT

Medical devices are provided that include at least one layer that defines a proximal end, a distal end, and an expanded volume portion between the proximal and distal ends. The expanded volume portion defines a longitudinal axis extending between the proximal and distal ends. A first end feature including a reversible connection for attachment to a pusher member may be attached to the proximal end. The first end feature may define a first axis between its opposing ends. Similarly, a second end feature defining a second axis between its opposing ends may be located at the distal end. In the contracted state (e.g., when constrained within a delivery catheter), the first axis and the second axis may be aligned with the longitudinal axis, and in the expanded state (e.g., when deployed), the first axis and/or the second axis may be angled with respect to the longitudinal axis.

38 Claims, 12 Drawing Sheets

(56) References Cited

U.S. PATENT DOCUMENTS

| | | |
|---|---|---|
| 2009/0062841 A1 | 3/2009 | Amplatz et al. |
| 2009/0099647 A1 | 4/2009 | Glimsdale et al. |
| 2009/0171386 A1 | 7/2009 | Amplatz et al. |
| 2009/0275974 A1 | 11/2009 | Marchand et al. |
| 2009/0287294 A1* | 11/2009 | Rosqueta et al. ............ 623/1.15 |
| 2010/0121370 A1 | 5/2010 | Kariniemi |
| 2010/0211046 A1 | 8/2010 | Adams et al. |
| 2011/0054519 A1 | 3/2011 | Neuss |
| 2011/0152993 A1 | 6/2011 | Marchand et al. |

\* cited by examiner

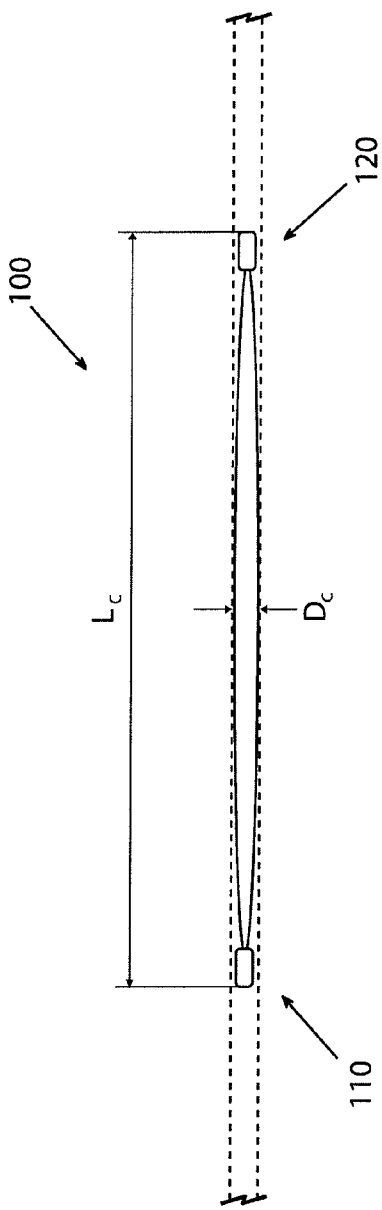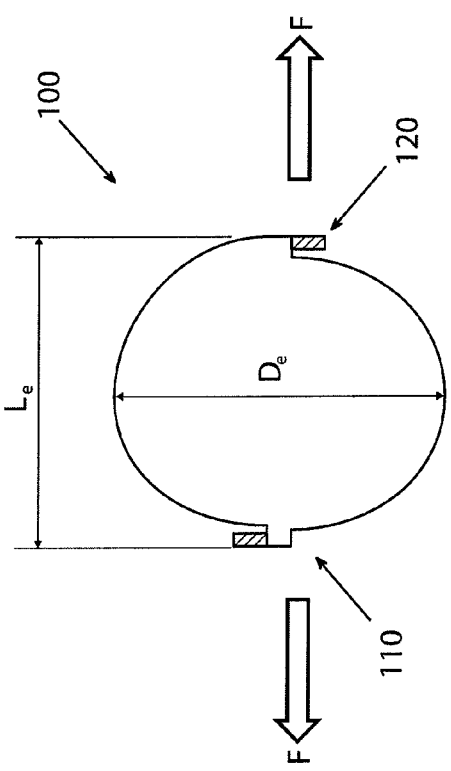

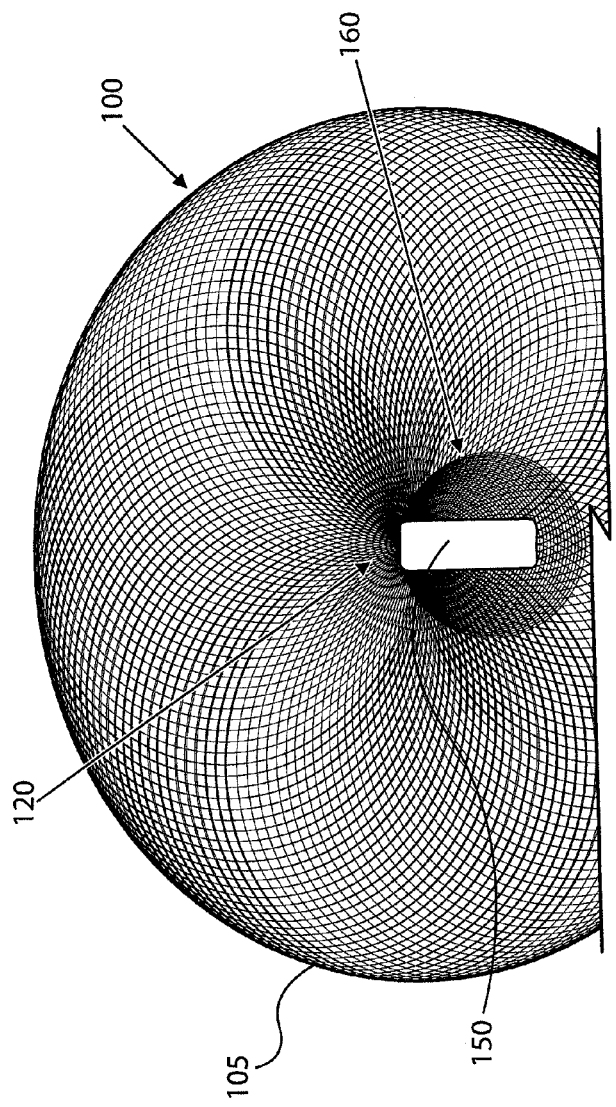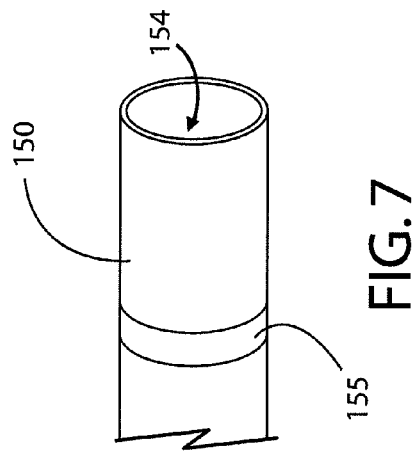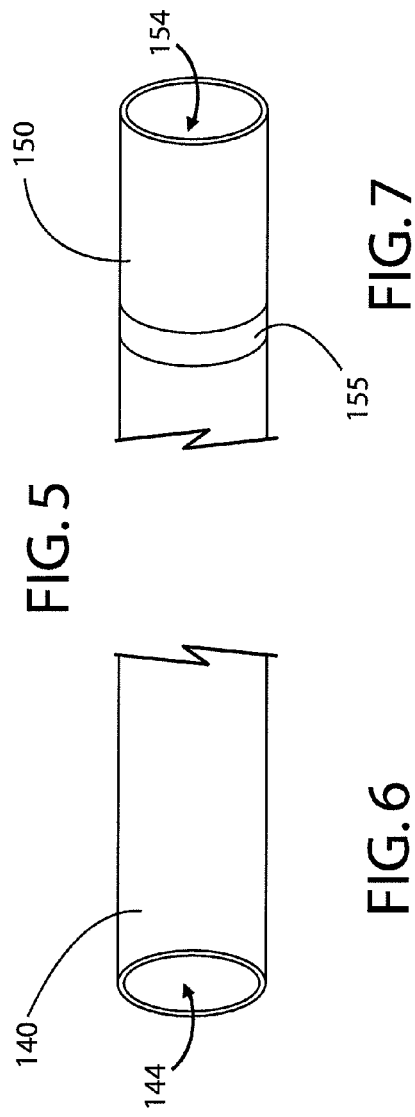
FIG. 5
FIG. 6
FIG. 7

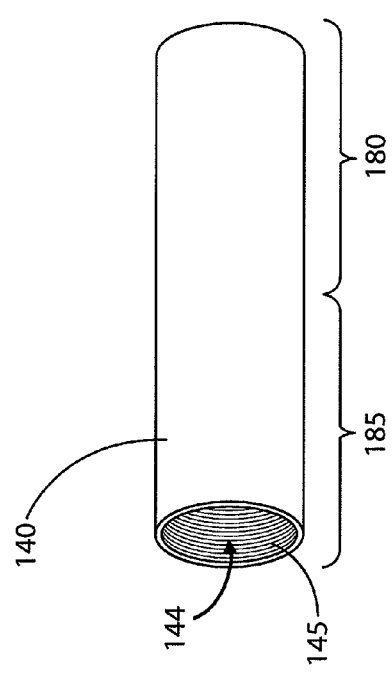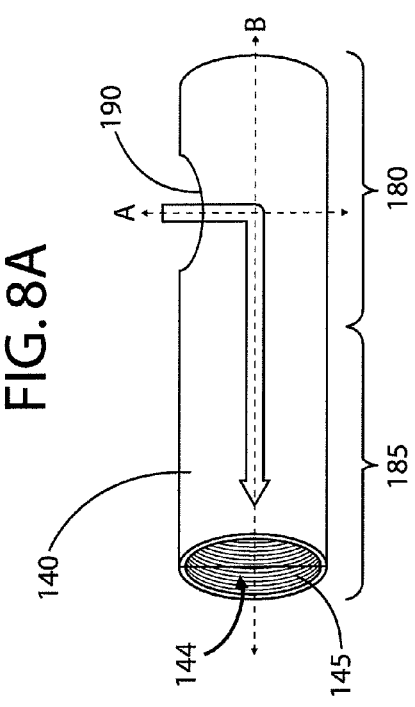

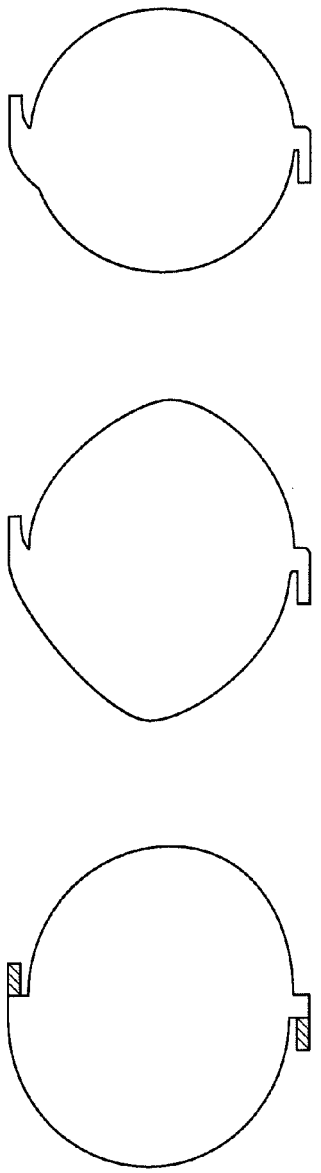
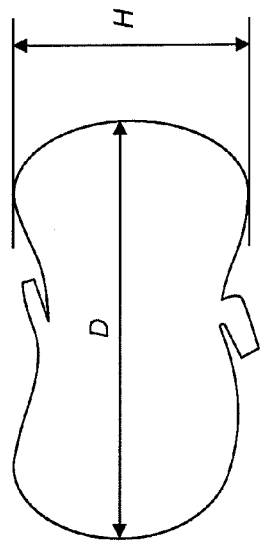
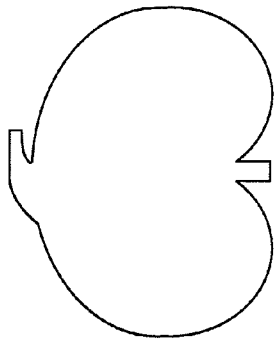
FIG. 10C
FIG. 10E
FIG. 10B
FIG. 10A
FIG. 10D

DEVICES AND METHODS FOR OCCLUDING VASCULAR ABNORMALITIES

BACKGROUND

I. Field of the Invention

Embodiments of the present invention relate generally to medical devices for treating certain vascular abnormalities, such as aneurysms. In particular, embodiments are directed to medical devices and methods for occluding vascular abnormalities in areas of a patient's neuro-vasculature such as the carotid artery.

II. Description of the Related Art

Various types of intravascular medical devices, both biological and synthetic, have been used for a large array of reparative vascular procedures, such as to treat obstructive vessels and aneurysms. An aneurysm, for example, is an abnormal widening or ballooning of a portion of an artery due to damage to or weakness in the wall of the blood vessel. Weaknesses in the blood vessel wall may be caused by medical conditions, such as arteriosclerosis, or may be congenital. As blood flows past the weakened area, the affected vessel wall thins over time and expands like a balloon, which can eventually burst if the vessel wall gets too thin.

The goal of therapy for aneurysms is to prevent the blood vessel from rupturing. Once an aneurysm has ruptured, for example in arteries leading to the brain, a stroke may occur and brain damage or even death may result if the patient does not receive immediate treatment. Brain damage or death may be avoided, however, if the aneurysm is detected and treated at an early stage, ideally when the aneurysm is relatively small, using a lower risk procedure.

Aneurysms may be treated with surgery. The surgical procedure for treating some types of aneurysms involves replacing the affected portion of the blood vessel with a synthetic graft, which may comprise a tube made out of an elastomer or polymer material with properties that are intended to substitute the function of a normal, healthy vessel. Due to limitations in reaching certain brain aneurysms, however, surgical treatment may not be an option. Moreover, even in accessible areas, surgical treatment is still complex and may pose additional risks to the patient, especially for the elderly.

More recently, instead of performing surgery to repair an aneurysm, an intravascular medical device, such as an endovascular stent or stent-graft, may be delivered to the site of the aneurysm using an elongated catheter. In other cases, the aneurysm may be filled with metallic coils or other embolic materials that are delivered through small catheters to cause clot formation and tissue growth within the aneurysm and to strengthen the wall and reduce the effect of blood pressure on the wall of the aneurysm, thereby reducing the likelihood of rupture. An endovascular stent-graft, for example, is a tube that includes a blood-impervious fabric supported by a metal stent. It can be used to treat a variety of conditions involving blood vessels, but most commonly is used to reinforce a vessel wall at the site of an aneurysm.

Depending on the size, shape, and location of the aneurysm various types of medical devices may be required to reinforce the vessel wall. For example, aneurysms occurring in the carotid artery may not allow for a sufficient "landing zone" proximal to and distal from the ends of the stent-graft for proper placement and maintaining of the medical device in position.

Aneurysms can be defined as wide-necked or narrow-necked aneurysms. Current therapies for treating wide-necked aneurysms include placing a stent over the lesion and introducing coils into the aneurysm. The stent acts as a gate and prevents the coils from falling out as there is minimal neck present. Some aneurysms, known as "berry" aneurysms, are very small and spherical in shape. Berry aneurysms typically have a narrow neck and often occur near or at a branch of an artery. Conventional methods of filling these aneurysms have limitations. For example, small metallic coils may not adequately fill the aneurysm and may embolize or protrude into the native vessel. Over-filling the aneurysm may further weaken the aneurysm. Liquid embolics that solidify in blood may also embolize or inadequately fill or seal the aneurysm, and the solidification process may release chemicals into the blood stream.

Accordingly, there is a need for an improved medical device designed to address vascular aneurysms, and particularly neuro-vascular aneurysms such as berry aneurysms in locations such as the carotid artery, the basilar artery, the Circle of Willis, the maxillary artery, the facial artery, and the vertebral artery that is capable of being deployed using smaller-diameter delivery devices, that is flexible enough for delivery through tortuous sections of vasculature, that provides effective and rapid exclusion at the target site, that is able to maintain its vascular position, that does not interfere with the normal flow of blood, and that overcomes the shortcomings of conventional solutions.

SUMMARY OF THE INVENTION

Embodiments therefore provide a medical device for occluding vascular abnormalities. In general, the medical device is configured such that at least one end of the device is at an angle to a longitudinal axis of an expanded volume portion of the device. In this way, the angled end may cause less trauma to the vascular wall at the site of the abnormality, and the shape of the device may be more easily accommodated by the abnormality.

In one embodiment, a device is provided that comprises at least one layer of fabric defining a proximal end, a distal end, and an expanded volume portion between the proximal and distal ends. The expanded volume portion may define a longitudinal axis extending between the proximal and distal ends. The device may further include a first end feature attached to the proximal end of the at least one layer, and the first end feature may define opposing ends and may further define a first axis extending between the opposing ends. A second end feature may be disposed at the distal end of the at least one layer, and the second end feature may define opposing ends and may further define a second axis extending between the opposing ends. The at least one layer may be configured to self-expand from a contracted state when constrained within a delivery catheter toward an expanded state when deployed from the delivery catheter for delivery to a target site within the body lumen. In the contracted state, each of the first axis and the second axis may be substantially aligned with the longitudinal axis and, in the expanded state, at least one of the first axis or the second axis may be different from the longitudinal axis and may define a preset angle with the longitudinal axis.

In some cases, the at least one layer of fabric may comprise a plurality of braided strands. The strands may have free ends, and at least one of the first or second end features may be configured to secure together the free ends of the strands at a respective proximal or distal end of the at least one layer. Additionally, each of the first and second end features may be configured to secure together the free ends of the strands at respective proximal and distal ends of the at least one layer of fabric. The at least one layer of fabric may comprise at least one metal selected from the group consisting of steel, stainless steel, shape memory alloy, and elastic alloy. In some cases, the at least one layer of fabric may comprise a polymer.

The at least one layer of fabric may comprise a first layer and a second layer, and the second layer may be disposed within, adjacent to, or surrounding the first layer. The second layer may comprise an elastomeric coating disposed adjacent the first layer. The first layer may, in some cases, be an inner layer, and the second layer may be an outer layer. The inner layer may define a first pick count and the outer layer may define a second pick count. The second pick count may be different from the first pick count. The relationship between the reduction in diameter and the elongation of the inner layer may be substantially the same as the relationship between the reduction in diameter and the elongation of the outer layer as the medical device is moved between the expanded state and the contracted state.

In some embodiments, the first end feature may comprise a reversible connection configured to engage a pusher member of the delivery catheter for advancing the medical device to the target site. Furthermore, the first end feature may comprise a first portion and a second portion, where the first portion defines a cross hole that is substantially aligned with the longitudinal axis and the second portion defines a channel that is substantially aligned with the first axis. Each of the cross hole and the channel may be configured to receive the first end of the plurality of braided strands at least partially therethrough.

In the expanded state, the first axis may be substantially perpendicular to the longitudinal axis. The expanded volume portion may define a recess configured to at least partially receive the first end feature or the second end feature. In the expanded state, each of the first axis and the second axis may be different from the longitudinal axis and may define a preset angle with the longitudinal axis that is between approximately 70° and approximately 120°. For example, in the expanded state, each of the first axis and the second axis may be substantially perpendicular to the longitudinal axis.

The medical device may be configured to be deployed in an aneurysm defining a neck and a cavity such that the expanded volume portion of the at least one layer of fabric substantially conforms to the shape of the cavity of the aneurysm. The expanded volume portion of the at least one layer of fabric may comprise a body portion configured to be received within the cavity of the aneurysm and a leaflet portion configured to be received within the cavity of the aneurysm and disposed adjacent to the neck of the aneurysm in the expanded state. In some embodiments, the expanded volume portion may comprise at least one thrombogenic material. The thrombogenic material may comprise filaments and the filaments may be substantially aligned with the longitudinal axis in the contracted state.

The expanded volume portion of the medical device defines a spherical, semi-spherical, or ovaloid shape.

In still other embodiments, a method of making a medical device for placement in a body lumen is provided. The method may include braiding a plurality of strands to form at least one layer of fabric defining a proximal end, a distal end, and an expanded volume portion between the proximal and distal ends, wherein the expanded volume portion defines a longitudinal axis extending between the proximal and distal ends. The method may further include attaching a first end feature to the proximal end of the at least one layer, where the first end feature defines opposing ends and further defines a first axis extending between the opposing ends, and disposing a second end feature at the distal end of the at least one layer, where the second end feature defines opposing ends and further defines a second axis extending between the opposing ends. The at least one layer of fabric may be configured to self-expand from a contracted state when constrained within a delivery catheter toward an expanded state when deployed from the delivery catheter for delivery to a target site within the body lumen. In addition, at least one of the first end feature or the second end feature may be angularly biased with respect to the expanded volume portion, such that, in the expanded state, a respective one of the first axis or the second axis is different from the longitudinal axis of the at least one layer of fabric and defines a preset angle with the longitudinal axis In some cases, the method may further include heat setting at least the proximal end of the at least one layer to a predefined shape, such that the first end feature is angularly biased with respect to the longitudinal axis of the expanded volume portion. A first end feature may be provided having a channel defined therethrough, where the strands have free ends, and where attaching the first end feature comprises passing the free ends at least partially through the channel and securing together the first end feature and the free ends of the strands at the proximal end of the at least one layer of fabric. The first end feature may, in some cases, comprise a first portion and a second portion, the first portion defining a cross hole that is substantially aligned with the longitudinal axis and the second portion defining a channel that is substantially aligned with the first axis. The strands may have free ends, and attaching a first end feature to the proximal end of the at least one layer may comprise passing and securing respective free ends of the plurality of braided strands at least partially through the cross hole and at least a portion of the channel and securing the strands to the first end feature.

In some embodiments, braiding a plurality of strands to form at least one layer of fabric may comprise braiding at least one metal selected from the group consisting of steel, stainless steel, shape memory alloy, and elastic alloy. Braiding a plurality of strands to form at least one layer may comprise braiding a polymer.

Braiding the plurality of strands to form the at least one layer may comprise braiding a first set of strands to form a first layer and braiding a second set of strands to form a second layer, where the second layer is disposed within or surrounding the first layer. The first layer may define a first pick count and the second layer may define a second pick count, where the second pick count is different from the first pick count. Embodiments of the method may further include selecting the first and second pick counts such that the relationship between the reduction in diameter and the elongation of the first layer is substantially the same as the relationship between the reduction in diameter and the elongation of the second layer as the medical device is moved between the expanded state and the contracted state. The method may further comprise braiding the plurality of strands of the first layer at a first helix angle and braiding the plurality of strands of the second layer at a second angle, such that the relationship between the reduction in diameter and the elongation of the first layer is substantially the same as the relationship between the reduction in diameter and the elongation of the second layer as the medical device is moved between the expanded state and the contracted state.

In some embodiments, the method may further comprise applying an elastomeric coating to a surface of the at least one layer to form a second layer adjacent to the at least one layer. Additionally or alternatively, at least one of the first and second end features may be configured to prevent unraveling of the plurality of strands. In some cases, each of the first axis and the second axis may be different from the longitudinal axis of the body portion and may define an angle with the longitudinal axis when deployed from the delivery catheter. Both the first axis and the second axis may be substantially perpendicular to the longitudinal axis when deployed from the device.

The method may further comprise forming at least one recess in the at least one layer configured to receive at least a corresponding one of the first end feature or the second end feature. The method may further comprise defining a body portion configured to be received within the cavity of the aneurysm and defining a leaflet portion configured to be received in the cavity of the aneurysm and disposed adjacent to the neck of the aneurysm in the expanded state.

In still other embodiments, a method of delivering a medical device is provided. The method may include providing a medical device comprising at least one layer of fabric defining a proximal end, a distal end, and an expanded volume portion between the proximal and distal ends, where the expanded volume portion defines a longitudinal axis extending between the proximal and distal ends. The medical device may further include a first end feature attached to the proximal end of the at least one layer, where the first end feature defines opposing ends and further defines a first axis extending between the opposing ends, and a second end feature disposed at the distal end of the at least one layer, where the second end feature defines opposing ends and further defines a second axis extending between the opposing ends. The at least one layer may be configured to self-expand from a contracted state when constrained within a delivery catheter toward an expanded state when deployed from the delivery catheter for delivery to a target site within the body lumen. In addition, at least one of the first end feature or the second end feature may be angularly biased with respect to the expanded volume portion, such that, in the expanded state, a respective one of the first axis or the second axis is different from the longitudinal axis of the at least one layer and defines a preset angle with the longitudinal axis. The method may further include advancing the medical device through a body lumen toward an aneurysm and deploying the medical device within the aneurysm.

BRIEF DESCRIPTION OF THE DRAWINGS

The foregoing features and advantages of embodiments of the invention will become apparent to those skilled in the art from the following detailed description of a preferred embodiment, especially when considered in conjunction with the accompanying drawings in which like numerals in the several views refer to corresponding parts.

FIG. 2A is a schematic illustration of a medical device in a contracted state according to an exemplary embodiment;

FIG. 2B is a schematic illustration of the medical device of FIG. 2A in an expanded state according to an exemplary embodiment;

FIG. 5 is a schematic illustration of a distal end of a medical device in an expanded state defining a recess for receiving the second end feature of the medical device according to an exemplary embodiment;

FIG. 6 is a schematic illustration of part of a first end feature of a medical device according to an exemplary embodiment;

FIG. 7 is a schematic illustration of part of a second end feature of a medical device according to an exemplary embodiment;

FIG. 8A is a schematic illustration of a first end feature including a first portion defining a channel and a second portion in which the channel defines a reversible connection according to an exemplary embodiment;

FIG. 8B is a schematic illustration of a first end feature including a first portion defining a cross hole and a second portion including a channel defining a reversible connection according to an exemplary embodiment;

FIGS. 10A-10G are schematic cross-sectional representations of various configurations of medical devices according to various exemplary embodiments;

DETAILED DESCRIPTION

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Embodiments of medical devices and methods are described below that are generally configured for treating aneurysms in the carotid artery and other neural blood vessels. Embodiments of the medical device are generally configured to fit within the dome or cavity of an aneurysm to fill the aneurysm, while at the same time not preventing or obstructing the flow of blood through the main vessel adjacent to the location of the aneurysm.

Figure 1:
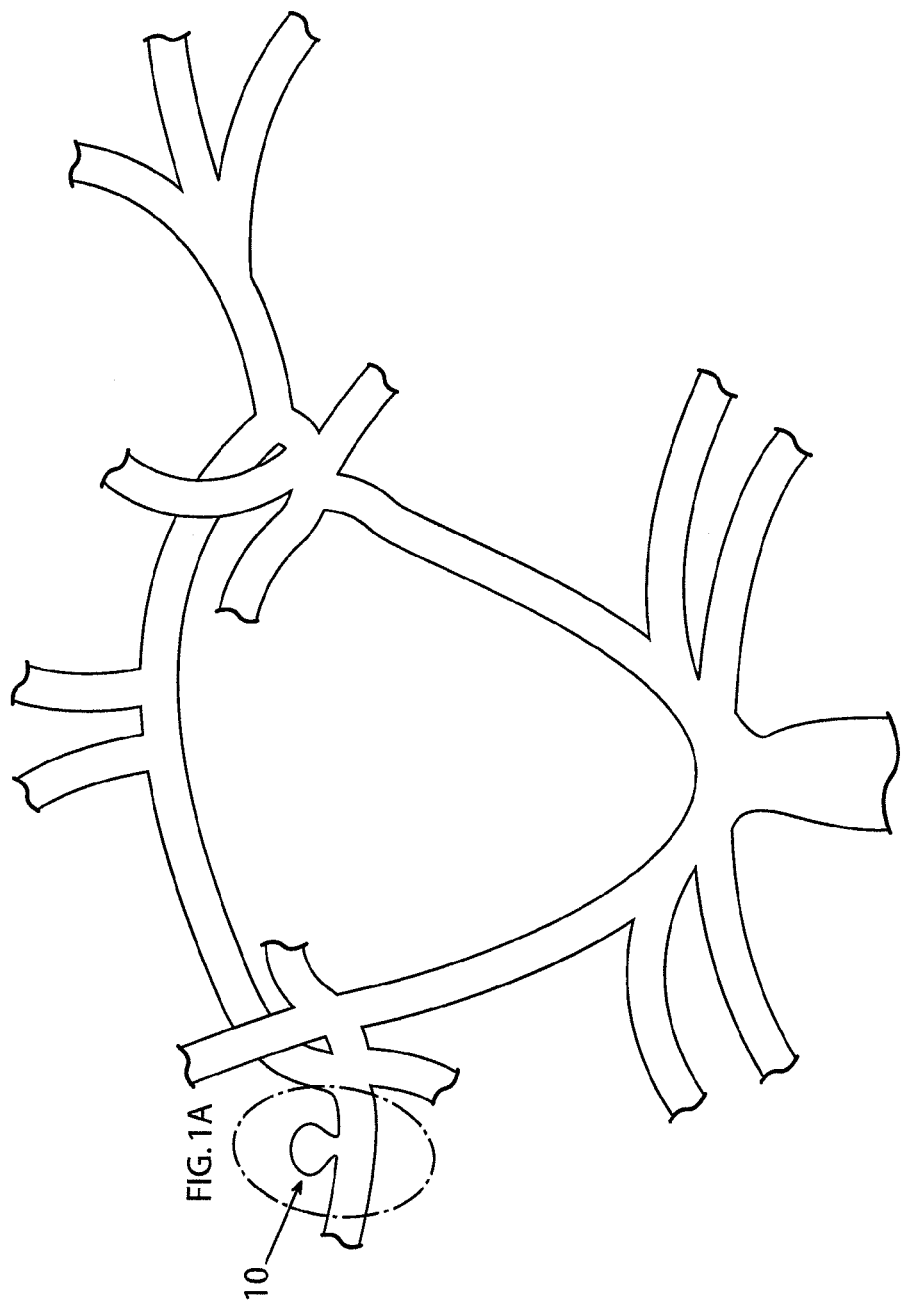
FIG. 1 is a schematic illustration of blood vessels in a patient's brain showing a berry aneurysm in the internal carotid complex.
Figure 1A:
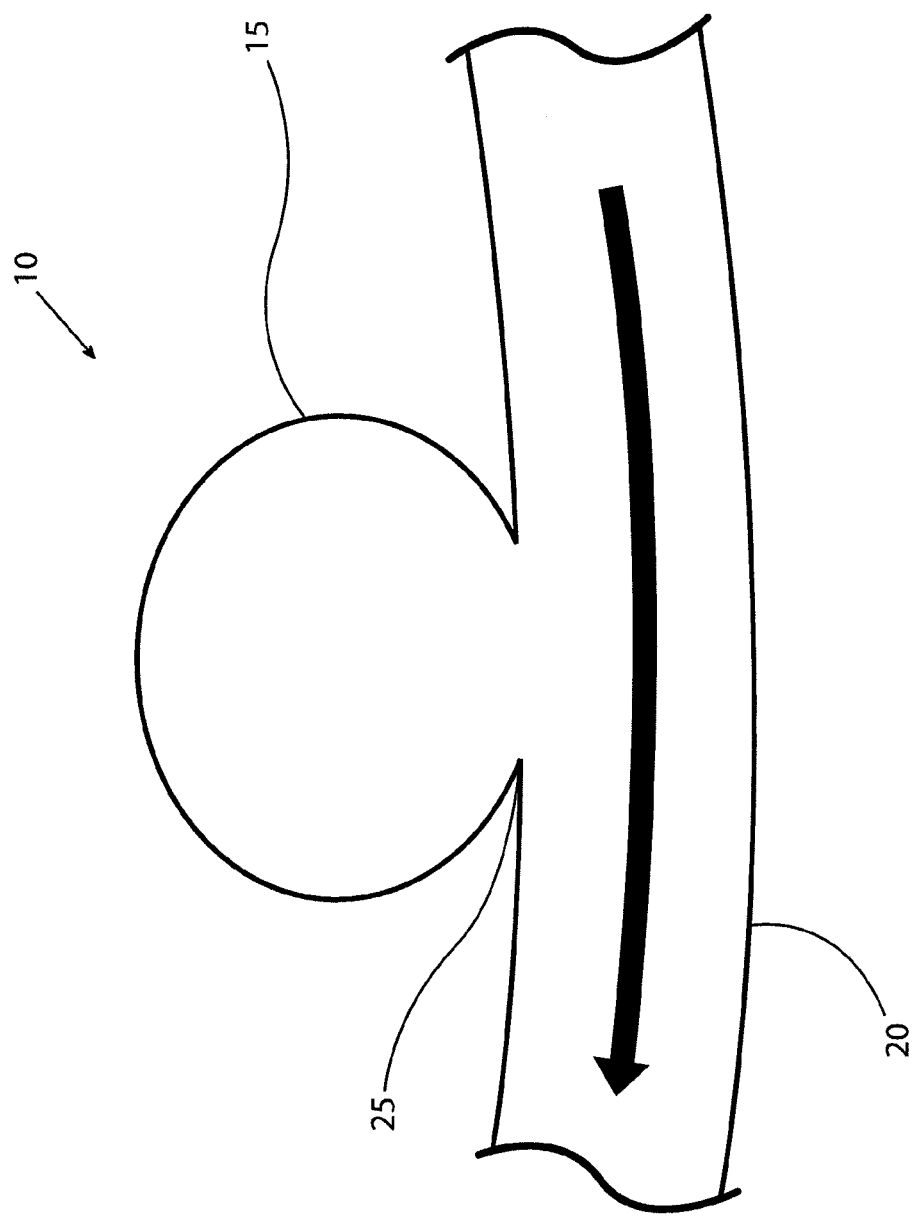
FIG. 1A is a close-up schematic illustration of the aneurysm of FIG. 1.

Turning to FIG. 1, for example, a berry aneurysm 10 located in the internal carotid complex is shown. The berry aneurysm 10, shown close-up in FIG. 1A, may include a cavity 15, or ballooned portion of the arterial wall 20, and a neck 25, which is the narrower portion of the aneurysm from which the cavity extends. If left untreated, blood flow past the aneurysm 10 would enter the cavity 15 via the neck 25 and apply pressure to the weakened walls of the vessel in the region of the aneurysm, expanding the aneurysm and increasing the risk that the aneurysm will rupture, causing serious problems for the patient such as a stroke and possibly resulting in brain damage or death.

The size, flexibility, and ability of the delivery catheter to navigate through tortuous vasculature to the site of a neuro-aneurysm are important considerations for selecting the delivery catheter when treating aneurysms. Delivery catheters used in the neuro-vasculature are typically referred to as micro catheters and are available in a variety of sizes from a number of vendors, such as Target Therapeutics, Inc. of Fremont, Calif. (owned by Stryker) and Cordis Corporation of Bridgewater, N.J. (a Johnson & Johnson company). For example, when the aneurysm is located in a distal vessel having a great deal of curvature and a small diameter and/or when the vessel diameter is reduced in size due to arteriosclerosis, larger delivery catheters may not be used or, at best, may cause trauma to the vascular tissue or may not be able to reach the aneurysm. Thus, the medical device used for treatment of the aneurysm must be low in profile and flexible enough to pass through the micro delivery catheters with adequate positional control to reach the target site of treatment and be deployed as desired to exclude the aneurysm. Accordingly, embodiments of the present invention provide for lower-profile medical devices. For example, embodiments of the present invention provide for a medical device that has a low profile, flexibility for delivery through a tortuous anatomy, low advancement force through the delivery catheter and positional control to deploy the device as desired to fill the aneurysm without obstructing normal flow, improved positional retention, lower risk of trauma to the aneurysm, ease of release of the medical device from the delivery system, and rapid exclusion of the aneurysm. For example, embodiments of the present invention provide for medical devices that have an expanded diameter in the range of about 3 Fr. to about 8 Fr., such that the medical devices can be delivered using micro catheters having a diameter of about 1.9 Fr. to about 2.8 Fr. nominal OD (0.023 inches ID to about 0.025 inches ID), although the outer diameter of these catheters can vary depending on flexibility requirements.

In addition, aneurysms may have different sizes and shapes depending on the patient, the location of the aneurysm, the cause of the aneurysm, and other factors. Accordingly, embodiments of the present invention are configured to self-expand from a contracted state when constrained within a delivery device (e.g., a micro catheter) toward an expanded state when deployed from the delivery device for delivery to the target site (e.g., the site of the aneurysm). In the expanded state, embodiments of the medical device are configured to fill and substantially conform to the shape of the cavity 15 of the aneurysm, causing thrombosis within the cavity and thereby precluding or at least minimizing the blood flow into the cavity to avoid expansion of the aneurysm and further damage to the patient's vasculature. At the same time, embodiments of the medical device are configured to minimize any localized trauma or pressure on the wall of the cavity 15 of the aneurysm and to minimize obstruction of the main pathway of blood flow through the vessel past the site of the aneurysm (shown by the arrow in FIG. 1A), as described below.

It is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to occlude or otherwise treat a variety of vascular abnormalities. For example, the vascular abnormality could be any abnormality that affects the shape of the native lumen, such as an aneurysm, a rupture, a vessel dissection, or a tumor. Embodiments of the medical device may be useful, for example, for treating an aneurysm in the vessels of a patient's neck and head. Furthermore, the term "lumen" is also not meant to be limiting, as the vascular abnormality may reside in a variety of locations within the vasculature, such as a vessel, an artery, a vein, a passageway, an organ, a cavity, or the like. For ease of explanation, the examples used herein refer to an aneurysm.

Figure 3A:
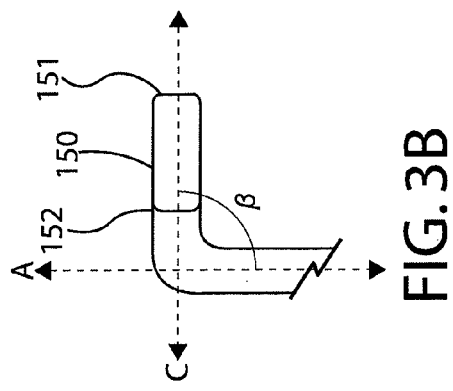
FIG. 3A is a close-up view of the proximal end of the medical device of FIG. 3.
Figure 3B:
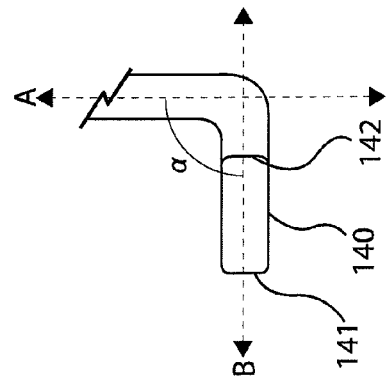
FIG. 3B is a close-up view of the distal end of the medical device of FIG. 3.
Figure 3:
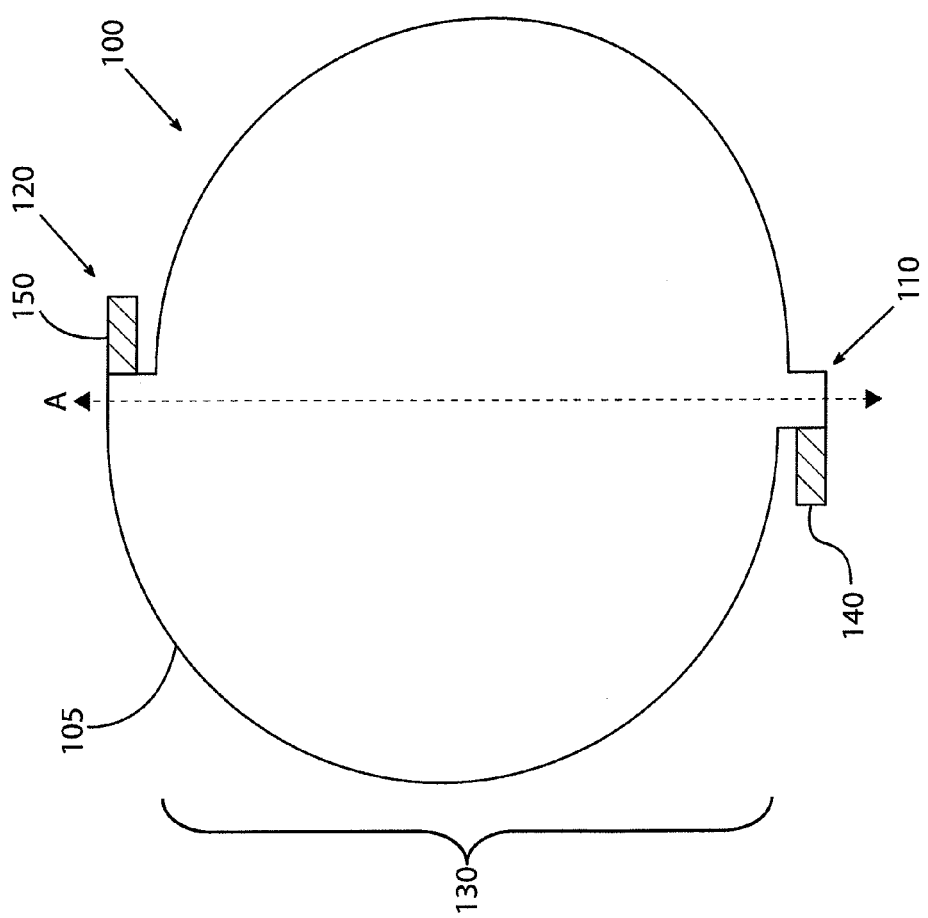
FIG. 3 is an illustration of a medical device in an expanded state according to an exemplary embodiment.

Turning now to FIG. 3, one embodiment of a medical device 100 that is configured to treat an aneurysm having a substantially spherical or ovaloid shape is shown. The medical device 100 comprises at least one layer 105 defining a proximal end 110 and a distal end 120. An expanded volume portion 130 is defined between the proximal and distal ends, and the expanded volume portion defines a longitudinal axis A extending between the proximal and distal ends 110, 120. As used herein, the term "proximal" refers to a part of the medical device 100 or the delivery device that is closest to the operator, and the term "distal" refers to a part of the medical device or the delivery device that is farthest away from the operator at any given time as the medical device is being delivered through the delivery catheter.

The medical device 100 may be configured to be moved between a contracted state when constrained within a delivery catheter (such as a micro catheter, represented by dashed lines in FIG. 2A) and an expanded state when deployed from the delivery catheter (FIG. 2B). In the contracted state, the medical device 100 may define a length $L_c$, and in the expanded state (FIG. 2B) defining a length $L_e$. The medical device 100 may be moved to the contracted state, for example, when the ends 110, 120 of the device are pulled away from each other and/or a radial constraint is applied to the device. In other words, as shown in FIG. 2B, the application of a tensile force F on the ends of the device 100 may serve to axially elongate and collapse the outer diameter $D_e$ of the device such that it may achieve a reduced diameter $D_c$, allowing the device to be received within a lumen of a delivery catheter in the contracted state (FIG. 2A) for delivery to the target site. Thus, in this example, the delivery device (e.g., a catheter) applies the radial constraint to maintain the medical device 100 in the contracted state.

The medical device 100 may be configured, however, such that, when the radial constraint is removed, the device can self-expand to the expanded state shown in FIG. 2B. For example, as the medical device 100 is unsheathed from the delivery catheter, portions of the medical device that are no longer constrained by the delivery catheter may self-expand and freely return to the expanded state, and once the medical device has been fully deployed from the delivery catheter proximate the target site, the medical device will at least partially assume the expanded state. For example, the vessel diameter may limit complete return to the expanded state.

Thus, a medical device having a predetermined shape may be collapsed by longitudinally stretching the medical device (as illustrated in FIG. 2A) for inserting the device into the lumen of a delivery catheter (e.g., a micro catheter, a guide catheter, or delivery sheath). The delivery catheter may then be positioned and advanced in a patient's body such that the distal end of the delivery catheter is adjacent to the target site (e.g., positioned at the neck 25 of the aneurysm). The medical device may be advanced through the delivery catheter such that the distal end of the medical device is near the distal end of the delivery catheter. Thus, as the medical device is deployed from the distal end of the delivery catheter, the diameter of the medical device is allowed to self-expand inside the cavity 15 of the aneurysm 10 to fill in the cavity.

Referring now to FIG. 2A, once the delivery catheter is in position at the target site, the medical device may be urged through the delivery catheter and out the distal end of the delivery catheter, whereupon it may substantially return to its expanded state (as illustrated in FIG. 2B). The delivery catheter may then be removed from the patient's body, leaving the medical device positioned at the target site.

Referring to FIG. 3 and FIG. 3A, a first end feature 140 may be attached to the proximal end 110 of the layer 105. The first end feature 140 may be configured to reversibly connect to a delivery catheter (not shown). For example, the first end feature may be a tubular structure defining opposing ends 141, 142 and may further define a first axis B extending between the opposing ends. Similarly, a second end feature 150 may be located at the distal end 120 of the layer 105. The second end feature may, in some cases, be a tubular structure, and in other cases may be a weld, a clamp, a layer of adhesive, or any other structure or method for holding together the wire ends at the distal end 120 of the layer 105. The layer 105 may be configured to self-expand from a contracted state when constrained within a delivery catheter toward an expanded state when deployed from the delivery catheter for delivery to a target site within the body lumen. In the contracted state, the first axis B may be aligned with the longitudinal axis A, and in the expanded state, the first axis B may be different from the longitudinal axis A and may, thus, define a preset angle a with the longitudinal axis.

Figure 4:
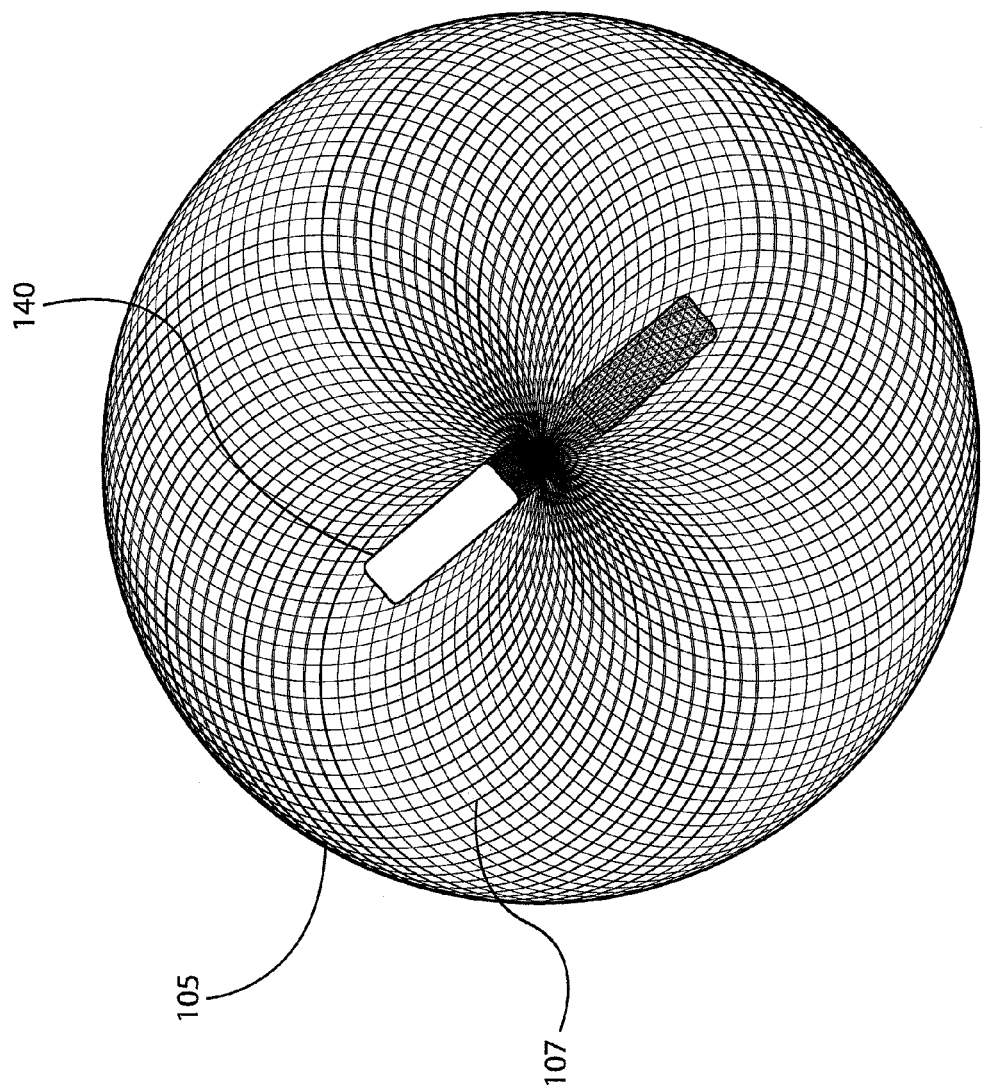
FIG. 4 is a perspective view of an end of a medical device including at least one layer of braided strands according to an exemplary embodiment.

With reference to FIG. 4, for example, the one or more layers 105 may be formed by braiding, interweaving, knitting, or otherwise combining filamentary materials together, such as by using a conventional tubular braiding machine. These filamentary materials may include, for example, fibers, thread, yarn, cable, metallic wires, polymer monofilament or multifilament strands, and combinations of these materials, any of which are referenced herein as "strands," and such terms may be used interchangeably. The strands 107 may be comprised of any material, such as natural materials, polymers, metals, metallic alloys, or combinations of the same. The strands may be braided to have a predetermined pick and pitch to define openings or fenestrations so as to vary the impedance of blood flow therethrough.

In some applications, wire strands may be used. The wire strands may be formed of a material that is both resilient and can be heat treated to stabilize the medical device 100 or a portion thereof (e.g., to substantially set a desired shape or braid pattern). For example, the proximal end 110 may be heat set to a predefined shape, such that the first end feature 140 is angularly biased with respect to the expanded volume portion 130. In other words, as a result of heat setting, the proximal end 110 may achieve a preset shape (as shown in FIG. 3A) such that when the first end feature 140 is attached to the proximal end, the opposing ends 141, 142 of the end feature may define a first axis B that is at a preset angle a with respect to the longitudinal axis once the medical device 100 has been allowed to self-expand and is no longer in the contracted state, as described above. In some embodiments, the preset angle α is an angle greater than approximately 60°, such as an angle between approximately 70° and approximately 135°.

The distal end 120 may additionally or alternatively be heat set to a predefined shape such that the second end feature 150 is angularly biased with respect to the expanded volume portion 130. Thus, in some embodiments, illustrated in FIG. 3B, the second end feature 150 may define opposing ends 151, 152 (e.g., opposing ends of a tubular structure or weld formation) and may further define a second axis C extending between the opposing ends of the second end feature, such that, in the expanded state, the second axis C is different from the longitudinal axis A and defines a preset angle β with the longitudinal axis. In some embodiments, the preset angle β is an angle greater than approximately 60°, such as an angle between approximately 70° and approximately 135°. In this regard, one or both of the proximal and distal ends 140, 150 may be heat treated such that they are able to achieve a set shape (e.g., the preset angle) while minimizing the compression resistance of the medical device as it is moved between the contracted state and the expanded state. For example, this may be achieved by heat setting one or both ends at a temperature of approximately 460-470° C. for about 5 minutes to set the shape and then air-cooling the ends.

In some cases, the first axis B may be substantially perpendicular to the longitudinal axis A in the expanded state, as shown in FIG. 3A. Similarly, the second axis C may be substantially perpendicular to the longitudinal axis A in the expanded state, as shown in FIG. 3B. Thus, in the expanded state, each of the first axis B and the second axis C may, in some embodiments, be substantially perpendicular to the longitudinal axis. In some cases, the first and second axes B, C may be oriented such that the first and second end features 140, 150 are pointing in substantially opposite directions, as shown, for example, in FIG. 3.

By having the proximal end 110 angled with respect to the longitudinal axis A, the proximal end and the first end feature 140 may be maintained in closer proximity to the wall of the vessel 20 near the neck 25 of the aneurysm 10 (FIG. 1A) and may, thus, protrude less into the pathway of blood flow past the aneurysm, thereby minimizing the obstruction of blood flow through the vessel. At the same time, the risk of migration or movement of the medical device 100 within the aneurysm 10 as a result of the force of the blood flow acting upon portions of the medical device in its path may be minimized. In addition, the angle of the first end feature may help the medical practitioner to orient the medical device within the aneurysm, such that the region of the medical device proximate the proximal end (where the highest density of braided strands may be found) may be aligned with the neck of the aneurysm, thereby providing the most support to this area of the vessel wall.

Angling of the distal end 120 with respect to the longitudinal axis A in the expanded state may allow the medical device 100 to better conform to the shape of the cavity 15 of the aneurysm 10 and may minimize trauma to the aneurysm and/or the risk of rupture. In other words, by providing for the distal end 120 and/or the second end feature 150 to be maintained proximate the expanded volume portion 130 through the angle β (rather than extending out from the expanded volume portion in alignment with the longitudinal axis A), localized pressure that may otherwise have resulted from the contact of the distal end 120 and/or the second end feature 150 with the wall of the cavity 15 may be minimized.

To further conform the profile of the first or second end features 110, 120 1to the shape of the expanded volume portion 130 when the medical device 100 is in the expanded state, the at least one layer 105 may define one or more recesses 160 configured to at least partially receive the first end feature 140 and/or the second end feature 150, as shown in FIG. 5. In this way, the angular bias of the first and/or second end feature 140, 150 may serve to move the first or second end feature, respectively, to a "tucked in" position, in which the respective end feature is at least partially received within the recess 160 when the medical device 100 is in the expanded state.

The first end feature 140 and/or the second end feature 150 may each define a channel 144, 154 therethrough for receiving free ends of the strands 107. In this way, the first end feature 140 and/or the second end feature 150 may be configured to secure together the free ends of the strands 107 at respective proximal or distal ends of the at least one layer. FIG. 6, for example, shows a first end feature 140 that defines the channel 144 therethrough. The first and/or second end features 140, 150 may, for example, be cylindrical in shape with opposing open ends. As such, the first end feature 140 and/or the second end feature 150 may be configured to prevent the unraveling of the plurality of strands 107 that form the one or more layers 105.

Moreover, in some embodiments, the first end feature 140 may comprise a reversible connection configured to engage a pusher member (e.g., a pusher wire or a pusher tube) for advancing the medical device 100 to the target site through the delivery catheter. In this regard, the first end feature 140 may define a first portion 180 and a second portion 185, shown in FIG. 8A. The first portion 180 may be configured to receive the free ends of the strands forming the at least one layer of the medical device and may be configured to hold the free ends together by clamping, welding, soldering, brazing, or otherwise adhering them to each other and/or to the first portion of the first end feature 140. The second portion 185 of the first end feature 140 may, in turn, include internal threads 145 defined on the inner surface of the channel 144, and the threads 145 may be configured to engage external threads defined on the outside surface of a pusher wire (not shown) of the delivery catheter for delivering the medical device 100. Thus, in some embodiments, the first end feature 140 may comprise a reversible connection configured to engage a pusher wire for advancing the medical device 100 to the target site through the delivery catheter. Other reversible connection means, such as wires or snares, may also be used. Although in the depicted embodiments the pusher wire includes external threads and the end feature of the medical device includes internal threads, the location of internal and external threads may be reversed if desired.

With reference to FIG. 7, the second end feature 150 may itself comprise a radiopaque material, or a marker band 155 may be attached to the second end feature that is configured to facilitate placement of the medical device at the target site. For example, the marker band 155 may include a radiopaque material, such as platinum iridium, to allow a medical practitioner to view the location of the medical device 100 (and, more particularly, the location of the second end feature) within the body using fluoroscopy to facilitate proper delivery and positioning of the device.

In some cases, in addition to defining channels 144, 154, one or both of the first and second end features 140, 150 may include a first portion 180 and a second portion 185, shown in FIG. 8B, configured to define a pathway for effecting a preset angle of the respective end of the medical device. The first portion 180 may, for example, define a cross hole 190 (such as an opening or end slot) that is substantially aligned with the longitudinal axis A, and the second portion 185 may define the channel 144, which is substantially aligned with the first axis A (in the case of the first end feature 140), or the channel 154, which is substantially aligned with the second axis B (in the case of the second end feature 150). Each of the cross hole 190 and the channel 144, 154 may be configured to receive a respective end of the at least one layer of the medical device at least partially therethrough.

Figure 9A:
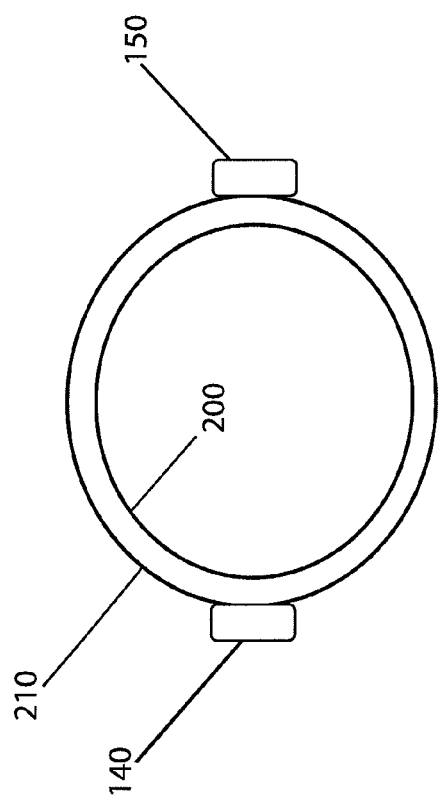
FIG. 9A is a schematic illustration of a medical device in an expanded state including a first layer and a second layer according to an exemplary embodiment.
Figure 9B:
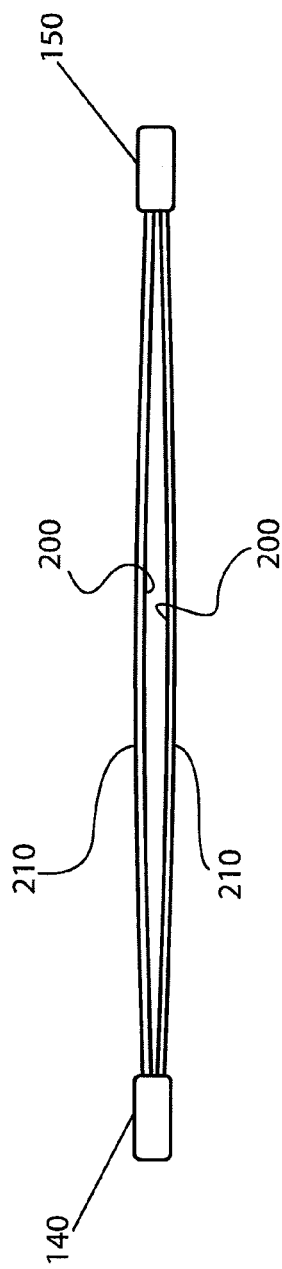
FIG. 9B is a schematic illustration of a medical device in a contracted state including a first layer and a second layer according to an exemplary embodiment.

In some embodiments, the at least one layer of the medical device may comprise a first layer 200 and a second layer 210, as illustrated in FIG. 9A (expanded state) and FIG. 9B (contracted state). One or both of the first and second layers 200, 210 may comprise a plurality of braided strands, as described above. Regardless of the number of layers, to facilitate delivery of the medical device to a target site in the body in a reduced profile configuration and also subsequently allowing the medical device to self-expand after being released from the constraint of the delivery catheter, the plurality of braided strands of the first layer and/or the plurality of braided strands of the second layer may include stainless steel, other metallic alloys, highly elastic alloys, and/or shape memory alloys, which are both resilient and can be heat treated to substantially set a desired shape. Exemplary suitable materials may include, for example, cobalt-based low thermal expansion alloys referred to as Elgiloy® Co—Cr—Ni alloy, nickel-based high temperature high-strength "superalloys" (for example, alloys commercially available from Haynes International under the trade name Hastelloy® alloy), nickel-based heat treatable alloys (for example, alloys commercially available from International Nickel under the trade name Incoloy® alloy) and a number of different grades of stainless steel.

In some embodiments, a factor in choosing a suitable material for the strands is the ability of the strands to retain a suitable amount of the deformation induced by the molding surface when subjected to a predetermined heat treatment, such as is exhibited by shape-memory alloys. One type of shape memory alloy is nickel-titanium (NiTi) alloy, called Nitinol alloy, which is also very elastic. In medical device applications, for example, this elasticity may allow a self-expanding medical device to return to a preset expanded configuration from a contracted configuration once it is deployed from a delivery catheter and is no longer constrained. Accordingly, in some embodiments, at least some of the strands comprise a shape memory alloy. Other materials having elastic properties may also be used, such as spring stainless steel and alloys such as Elgiloy®, Hastelloy®, Phynox®, MP35N®, and CoCrMo alloys.

In some instances, polymeric materials may also be used for the strands. Furthermore, polymeric materials may be combined with other materials in the formation of tubular structures for certain applications. For example, the medical device may include a combination of polyester yarn and stainless steel wire. Thus, in some embodiments, the plurality of braided strands of the first layer 200 may include Nitinol, and the plurality of braided strands of the second layer 210 may include a polymer. In other cases, materials may be used that are compatible with magnetic resonance imaging (MRI), considering that some materials may generate heat or experience torque as a result of undergoing MRI or may distort the MRI image. Thus, metallic and/or non-metallic materials that reduce or eliminate the potential problems resulting from the use of MRI may be used, depending on the application.

Further examples of materials and manufacturing methods for medical devices with shape memory properties are provided in U.S. Publication No. 2007/0265656 titled "Multi-layer Braided Structures for Occluding Vascular Defects" and filed on Jun. 21, 2007, which is incorporated by reference herein in its entirety.

Referring again to FIGS. 9A and 9B, the second layer 210 may be disposed within, adjacent to, or surrounding the first layer 200. In FIGS. 9A and 9B, for example, the second layer 210 is disposed adjacent to the first layer 200. Thus, as shown, the first layer 200 may be an inner layer and the second layer 210 may be an outer layer. The second layer 210 may completely surround the first layer 200, and the layers may have the same or similar shape as one another. In some embodiments, the pick count, or the number of strand crossings per unit length of the layers 200, 210, may be set at different predetermined values. For example, the inner layer (e.g., the first layer 200) may define a first pick count, and the outer layer (e.g., the second layer 210) may define a second pick count, where the second pick count is different from the first pick count.

Although the first pick count, as braided, may be different from the second pick count, as braided, the first and second pick counts may be selected such that the relationship between the reduction in diameter $d_1$ and the elongation $l_1$ of the inner layer (e.g., the first layer 200) is substantially the same as the relationship between the reduction in diameter $d_2$ and the elongation $l_2$ of the outer layer (e.g., the second layer 210). For example, a ratio of the decrease in diameter $d_1$ of the inner layer to the increase in length $l_1$ of the inner layer may be substantially the same as a ratio of the decrease in diameter $d_2$ of the outer layer to the increase in length $l_2$ of the outer layer. Thus, adjacent portions of the inner and outer layers (e.g., the first and second layers 200, 210, respectively) may remain in their relative adjacent positions as the medical device 100 moves between the expanded and contracted states. In this way, the inner layer and the outer layer of the medical device may cooperatively collapse and expand at generally the same rate, which enhances the stability of the medical device and facilitates its delivery into the vessel lumen and subsequent self-expansion.

Furthermore, the helix angle of the strands (e.g., the angle formed between the strand and the longitudinal axis of the braid mandrel as the strand is applied to the mandrel) used to braid the plurality of strands of the first and second layers 200, 210 may be different. The helix angles may be selected such that the plurality of strands of the first layer 200 is braided at a first helix angle, and the plurality of strands of the second layer 210 is braided at a second helix angle to ensure that the relationship between the reduction in diameter $d_1$ and the elongation $l_1$ of the first layer is substantially the same as the relationship between the reduction in diameter $d_2$ and the elongation of the second layer $d_2$ as the at least one layer is moved between the expanded state and the contracted state.

As noted above, the uniform movement that results between the first and second layers 200, 201 may thus reduce the risk of bunching or gathering of the layers within the medical device 100, which would otherwise reduce the effectiveness of the medical device by increasing its delivery profile and/or generating gaps between the various layers of material that may cause leaks.

In still other embodiments, the second layer 210 may comprise an elastomeric coating configured to speed up occlusion. The second layer 210 may be disposed such that the elastomeric coating is adjacent the first layer 200 and, in some cases, in contact with or coated upon the first layer.

Although the foregoing description uses the example of a medical device configured to have a shape, when in the expanded state, that substantially conforms to the shape of a substantially round aneurysm, various other shapes and configurations of medical devices are contemplated that include one or more of the features described in connection with FIGS. 2A-9B above, including spherical, semi-spherical, and/or ovaloid shapes. Examples of such medical devices are illustrated in FIGS. 10A-11B. For example, FIG. 10A depicts an ovaloid device; FIG. 10B depicts an ellipsoidal device; and FIG. 10C shows a round device. FIG. 10D illustrates a pumpkin-shaped device, where one of the end features defines an axis that is substantially aligned with (e.g., within 10° of) the longitudinal axis and the other end feature defines an axis that is at a preset angle (e.g., greater than 60° with respect to the longitudinal axis. FIG. 10E shows an apple-shaped device.

Figure 10F:
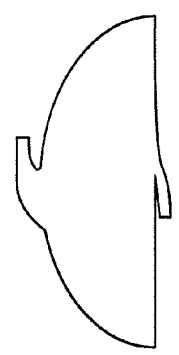
Figure 10G:
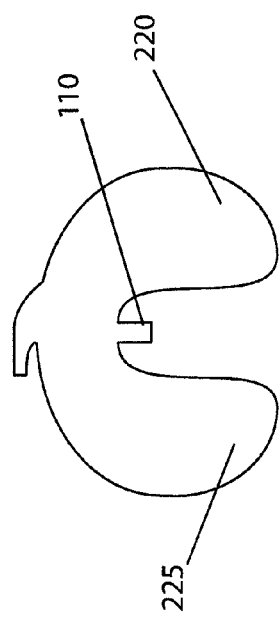

FIG. 10F depicts a medical device that is oversized such that, once inserted into the aneurysm, the portions 220, 225 will collapse inward (e.g., toward the proximal end 110) and substantially close off the neck of the aneurysm. In FIG. 10G, the medical device is configured for use in wide-neck aneurysms.

As described above, embodiments of the medical device are configured to be deployed in aneurysms defining a neck and a cavity (see, e.g., FIG. 1B), such that the expanded volume portion 130 of the at least one layer 105 substantially conforms to the shape of the cavity of the aneurysm. As such, the dimensions D and H shown in FIG. 10E, for example, may be varied, as needed, to produce the best fit of the medical device with the size and shape of the particular aneurysm. For example, in some embodiments, the dimension H is about 20%-30% smaller than the dimension D.

Figure 11B:
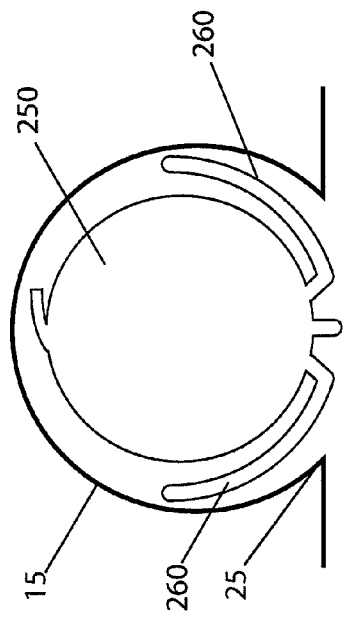
FIGS. 11A-11B are schematic cross-sectional representations of various configurations of medical devices including a body portion and a leaflet portion according to various exemplary embodiments.
Figure 11A:
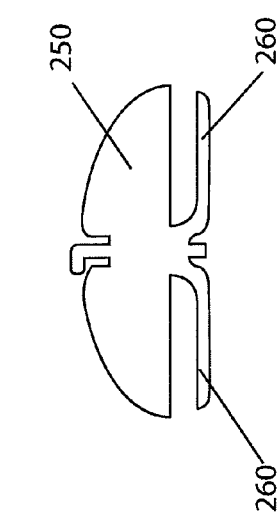

Turning now to FIGS. 11A and 11B, in some embodiments, the expanded volume portion of the at least one layer 105 may comprise a body portion 250 configured to be received within the cavity 15 of the aneurysm and a leaflet portion 260 configured to be received within the cavity 15 of the aneurysm and disposed adjacent to the neck 25 of the aneurysm in the expanded state. The leaflet portion 260 may, in the expanded state, have a width that is similar to or greater than the width of the body portion 250, such that the leaflet portion can conform to the size and shape of the neck 25 of the aneurysm. The leaflet portion 260 may, for example, have a curvature that approximates the curvature of the body portion 250 adjacent the leaflet portion (e.g., to substantially the adjacent part of the body portion, as shown in FIG. 11B) so as to anchor the medical device within the cavity 15 of the aneurysm and to provide adequate coverage of the neck 25 to minimize the flow of blood into the cavity. Moreover, the leaflet portions 260 may be configured to support and protect the neck 25 without applying localized forces that may cause trauma to the vessel in the area of the neck. Thus, as the medical device is deployed within the cavity 15, the self-expansion of the expanded volume portion and, more particularly, the body portion 250 of the medical device may serve to push the leaflet portions 260 out against the neck 25 from within the cavity, allowing better coverage of the neck and better preclusion of blood flow into the cavity (see, e.g., FIG. 11B).

In addition to adjustments in the configuration of the medical device, the flow of blood into the aneurysm may be further minimized by incorporating at least one thrombogenic material into the expanded volume portion of one or more layers of the medical device. Thus, in some cases, the expanded volume portion 130 (shown in FIG. 3, for example) may comprise at least one thrombogenic material. For example, the thrombogenic material may include filaments, such as polyester strands, that are randomly placed along the expanded volume portion 130. The strands may, for example, be woven into a fabric, for example, and the fabric may be sewn across an interior of the device, or individual strands may be incorporated in a particular pattern or randomly through the braided mesh of the expanded volume portion 130, such that the strands collapse when the medical device is in the contracted state and expand when the medical device is in the expanded state. Thus, the filaments may be substantially aligned with the longitudinal axis A in the contracted state. In some cases, the strands may be coated with a topical applicant, such as thrombin, silicone, or other materials having properties that initiate thrombosis. Regardless, the presence of the strands in the path of blood flow may create blood flow disturbance, which encourages the formation of clots and aids in the preclusion of blood flow into the aneurysm.

In one embodiment, the device may be shaped to have a 3 mm spherical diameter and may be comprised of a single layer of metal fabric. The single layer of metal fabric may be comprised of 72 strands of Nitinol wires (36 strands each braided in opposite helical directions) having a diameter of 0.001 inch. The strands may be braided into a tubular structure on a 6 mm diameter mandrel and may have a pick count of 100 picks per inch (PPI). The structure may be heat set using a spherically-shaped mold at approximately 460-470° C. for about 5 minutes to set the shape.

In another embodiment, a spherically-shaped device having an expanded diameter of 8 mm may comprise two fabric layers, and each fabric layer may comprise 72 Nitinol strands having a diameter of 0.001 inch. The strands may be braided into a tubular structure on a 10 mm diameter mandrel and may have a pick count of 125 PPI. The two layers may then be heat set on a spherically-shaped mold at approximately 505-515° C. for about 7.5 minutes.

The example embodiments provided above are not meant to limiting as to the wire diameter, pick count, numbers of layers, or number of wires or filaments that may be used in each layer, and these variables may be changes to achieve different properties of the devices as desired. For example, the wire diameter may vary from between about 0.0007 inch to about 0.003 inch; the number of braided strands per layer may vary from 36-144 strands or more in some cases; and the pick counts may vary from between about 60 to about 150 PPI.

A method for making a medical device for placement in a body lumen as described above is summarized in FIG. 12. The method includes braiding a plurality of strands to form at least one layer defining a first end, a second end, and an expanded volume portion between the proximal and distal ends. Block 300. As described above with reference to the figures, the expanded volume portion may define a longitudinal axis extending between the proximal and distal ends. A first end feature may be attached to the proximal end of the at least one layer at Block 310. The first end feature may define opposing ends and may further define a first axis extending between the opposing ends. A second end feature may be attached to the distal end of the at least one layer at Block 320. The second end feature may also define opposing ends and may further define a second axis extending between the opposing ends. The at least one layer may be configured to self-expand from a contracted state when constrained within a delivery catheter toward an expanded state when deployed from the delivery catheter for delivery to a target site within the body lumen. In addition, at least one of the first end feature or the second end feature may be angularly biased with respect to the expanded volume portion, such that, in the expanded state, a respective one of the first axis or the second axis may be different from the longitudinal axis of the at least one layer and may define a preset angle with the longitudinal axis.

In some embodiments, as described above, the proximal end of the at least one layer may be heat set to a predefined shape at Block 330, such that the first end feature is angularly biased with respect to the expanded volume portion. Additionally or alternatively, the distal end of the at least one layer may be heat set to a predefined shape at Block 340, such that the second end feature is angularly biased with respect to the expanded volume portion. The proximal and distal ends of the layer may be heat set at the same or different times, as well as the expanded volume portion. Blocks 350, 360.

Figure 13:
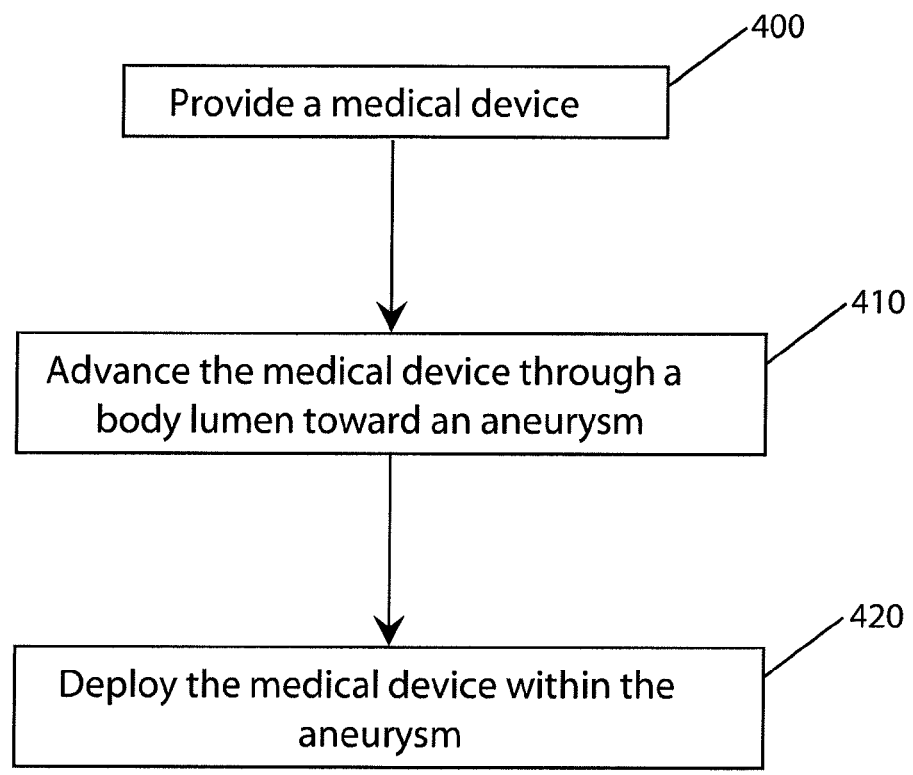
FIG. 13 illustrates a method for delivering a medical device according to an exemplary embodiment.

In FIG. 13, a method for delivering a medical device as described above is summarized. The method includes providing a medical device configured as described above in connection with one or more of FIGS. 2-11. Block 400. For example, the medical device may include at least one layer defining a proximal end, a distal end, and an expanded volume portion between the proximal and distal ends. The expanded volume portion may define a longitudinal axis extending between the proximal and distal ends. A first end feature may be attached to the proximal end of the at least one layer and may be configured to reversibly connect to a delivery catheter. The first end feature may define opposing ends and may further define a first axis extending between the opposing ends. A second end feature may be attached to the distal end of the at least one layer. The second end feature may also define opposing ends and may further define a second axis extending between the opposing ends. The at least one layer may be configured to self-expand from a contracted state when constrained within a delivery catheter toward an expanded state when deployed from the delivery catheter for delivery to a target site within the body lumen. At least one of the first end feature or the second end feature may be angularly biased with respect to the expanded volume portion, such that, in the expanded state, a respective one of the first axis or the second axis may be different from the longitudinal axis of the at least one layer and may define a preset angle with the longitudinal axis.

The method of delivery may further include advancing the medical device through the body lumen toward an aneurysm (Block 410) and deploying the medical device within the aneurysm (Block 420).

Figure 12:
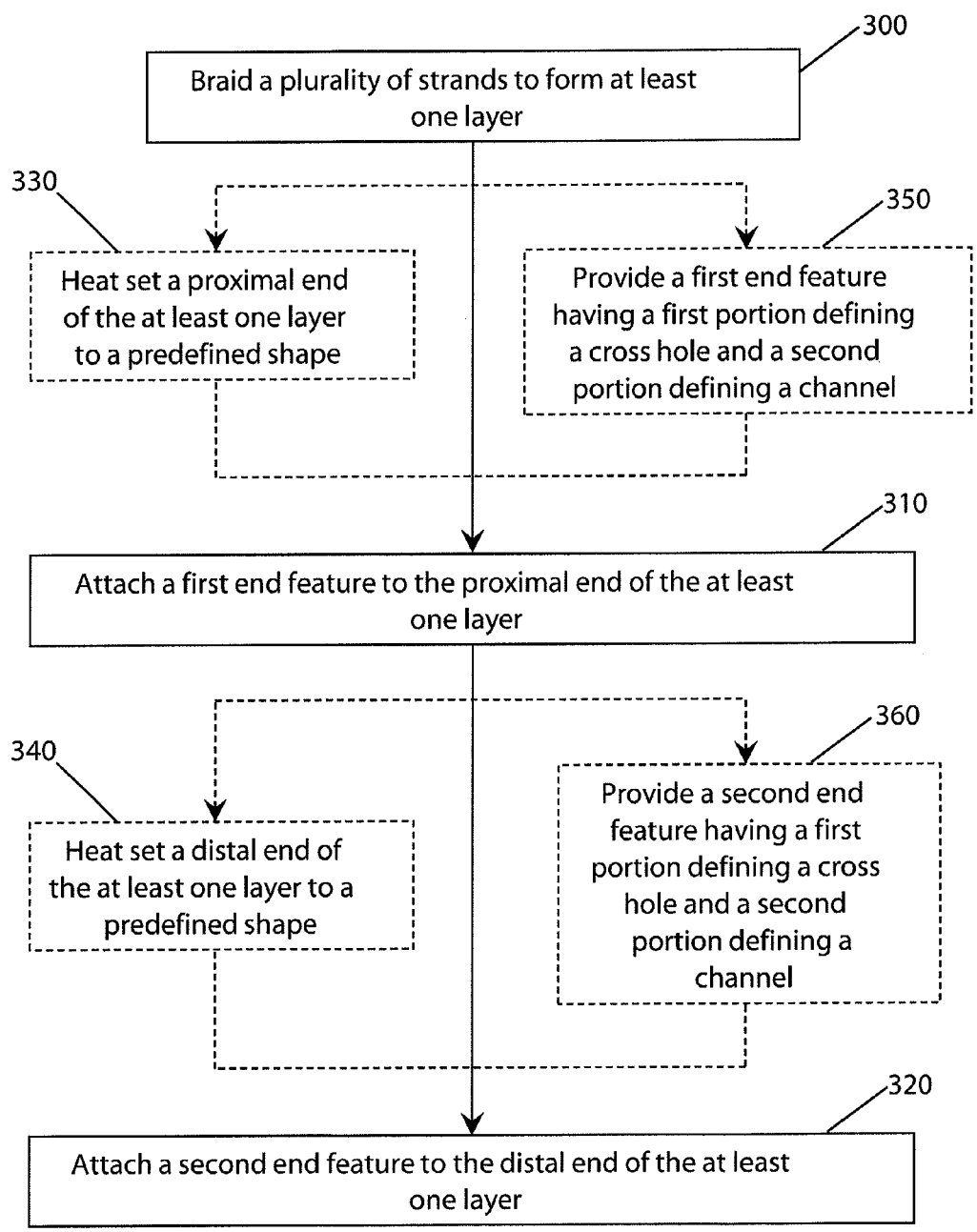
FIG. 12 illustrates a method for making a medical device for placement in the body lumen according to an exemplary embodiment.

The method depicted in FIG. 12 and described above represents only one method for making a medical device for placement in a body lumen. Similarly, the method depicted in FIG. 13 and described above represents only one method for delivering a medical device. In some embodiments, certain ones of the steps described above may be modified or further amplified. Furthermore, in some embodiments, additional optional steps may be included, some examples of which are shown in dashed lines in FIG. 12. Modifications, additions, or amplifications to the steps above may be performed in any order and in any combination. The particular methods of manufacturing and delivery will depend on the desired configuration of the medical device, the patient's anatomy, the condition and location of the target site, the preferences of the practitioner, and/or other considerations.

This invention has been described herein in considerable detail in order to comply with the Patent Statutes and to provide those skilled in the art with the information needed to apply the novel principles and to construct and use embodiments of the example as required. However, it is to be understood that specifically different devices can carry out the invention and that various modifications can be accomplished without departing from the scope of the invention itself. For example, options shown for one embodiment could easily be applied to other embodiments, as desired for a particular application, without departing from the scope of this invention.

That which is claimed:
1. A medical device comprising:
at least one layer of fabric defining a proximal end, a distal end, and an expanded volume portion between the proximal and distal ends, wherein the expanded volume portion defines a longitudinal axis extending between the proximal and distal ends;
a first end feature attached to the proximal end of the at least one layer, wherein the first end feature defines opposing ends and further defines a first axis extending between the opposing ends; and
a second end feature disposed at the distal end of the at least one layer, wherein the second end feature defines opposing ends and further defines a second axis extending between the opposing ends, wherein the at least one layer is configured to self-expand from a contracted state when constrained within a delivery catheter toward an expanded state when deployed from the delivery catheter for delivery to a target site within the body lumen, and wherein, in the contracted state, each of the first axis and the second axis is substantially aligned with the longitudinal axis and, in the expanded state, at least one of the first axis or the second axis is different from the longitudinal axis and defines a preset angle with the longitudinal axis.

2. The medical device of claim 1, wherein the at least one layer of fabric comprises a plurality of braided strands.

3. The medical device of claim 2, wherein the strands have free ends, and wherein at least one of the first or second end features is configured to secure together the free ends of the strands at a respective proximal or distal end of the at least one layer.

4. The medical device of claim 2, wherein the strands have free ends, and wherein each of the first and second end features is configured to secure together the free ends of the strands at respective proximal and distal ends of the at least one layer of fabric.

5. The medical device of claim 1, wherein the at least one layer of fabric comprises at least one metal selected from the group consisting of steel, stainless steel, shape memory alloy, and elastic alloy.

6. The medical device of claim 1, wherein the at least one layer of fabric comprises a polymer.

7. The medical device of claim 1, wherein the at least one layer of fabric comprises a first layer and a second layer, wherein the second layer is disposed within, adjacent to, or surrounding the first layer.

8. The medical device of claim 7, wherein the second layer comprises an elastomeric coating disposed adjacent the first layer.

9. The medical device of claim 6, wherein the first layer is an inner layer and the second layer is an outer layer, wherein the inner layer defines a first pick count and the outer layer defines a second pick count, and wherein the second pick count is different from the first pick count.

10. The medical device of claim 9, wherein the relationship between the reduction in diameter and the elongation of the inner layer is substantially the same as the relationship between the reduction in diameter and the elongation of the outer layer as the medical device is moved between the expanded state and the contracted state.

11. The medical device of claim 1, wherein the first end feature comprises a reversible connection configured to engage a pusher member of the delivery catheter for advancing the medical device to the target site.

12. The medical device of claim 1, wherein the at least one layer of fabric comprises a plurality of braided strands having free ends, wherein the first end feature comprises a first portion and a second portion, wherein the first portion defines a cross hole that is substantially aligned with the longitudinal axis and the second portion defines a channel that is substantially aligned with the first axis, wherein each of the cross hole and the channel is configured to receive a first end of the plurality of braided strands at least partially therethrough.

13. The medical device of claim 1, wherein, in the expanded state, the first axis is substantially perpendicular to the longitudinal axis.

14. The medical device of claim 1, wherein the expanded volume portion defines a recess configured to at least partially receive the first end feature or the second end feature.

15. The medical device of claim 1, wherein, in the expanded state, each of the first axis and the second axis is different from the longitudinal axis and defines a preset angle with the longitudinal axis that is between approximately 7020 and approximately 120°.

16. The medical device of claim 15, wherein, in the expanded state, each of the first axis and the second axis is substantially perpendicular to the longitudinal axis.

17. The medical device of claim 1, wherein the medical device is configured to be deployed in an aneurysm defining a neck and a cavity such that the expanded volume portion of the at least one layer of fabric substantially conforms to the shape of the cavity of the aneurysm.

18. The medical device of claim 17, wherein the expanded volume portion of the at least one layer of fabric comprises a body portion configured to be received within the cavity of the aneurysm and a leaflet portion configured to be received within the cavity of the aneurysm and disposed adjacent to the neck of the aneurysm in the expanded state.

19. The medical device of claim 1, wherein the expanded volume portion comprises at least one thrombogenic material.

20. The medical device of claim 19, wherein the thrombogenic material comprises filaments and the filaments are substantially aligned with the longitudinal axis in the contracted state.

21. The medical device of claim 1, wherein the expanded volume portion of the medical device defines a spherical, semi-spherical, or ovaloid shape.

22. A medical device comprising:
at least one layer of fabric comprising a plurality of braided strands having free ends, wherein the at least one layer of fabric defines a proximal end, a distal end, and an expanded volume portion between the proximal and distal ends, wherein the expanded volume portion defines a longitudinal axis extending between the proximal and distal ends;
a first end feature configured to secure together the free ends of the strands at the proximal end of the at least one layer, wherein the first end feature defines opposing ends and further defines a first axis extending between the opposing ends, and wherein one of the opposing ends is positioned proximate the proximal end of the at least one layer of fabric; and
a second end feature configured to secure together the free ends of the strands at the distal end of the at least one layer, wherein the second end feature defines opposing ends and further defines a second axis extending between the opposing ends, and wherein one of the opposing ends is positioned proximate the distal end of the at least one layer of fabric,
wherein the at least one layer is configured to self-expand from a contracted state when constrained within a delivery catheter toward an expanded state when deployed from the delivery catheter for delivery to a target site within the body lumen, and
wherein at least one of the first end feature or the second end feature is angularly biased with respect to the expanded volume portion, such that, in the expanded state, a respective one of the first axis or the second axis defines a preset angle with the longitudinal axis that is between approximately 7020 and approximately 120°.

23. The medical device of claim 22, wherein the at least one layer of fabric comprises a first layer and a second layer, wherein the second layer is disposed within, adjacent to, or surrounding the first layer.

24. The medical device of claim 23, wherein the first layer is an inner layer and the second layer is an outer layer, wherein the inner layer defines a first pick count and the outer layer defines a second pick count, and wherein the second pick count is different from the first pick count.

25. The medical device of claim 23, wherein the relationship between the reduction in diameter and the elongation of the inner layer is substantially the same as the relationship between the reduction in diameter and the elongation of the outer layer as the medical device is moved between the expanded state and the contracted state.

26. The medical device of claim 22, wherein the first end feature comprises a reversible connection configured to engage a pusher member of the delivery catheter for advancing the medical device to the target site.

27. The medical device of claim 22, wherein the first end feature comprises a first portion and a second portion, wherein the first portion defines a cross hole that is substantially aligned with the longitudinal axis and the second portion defines a channel that is substantially aligned with the first axis, wherein each of the cross hole and the channel is configured to receive a first end of the plurality of braided strands at least partially therethrough.

28. The medical device of claim 22, wherein the expanded volume portion defines a recess configured to at least partially receive the first end feature or the second end feature.

29. The medical device of claim 22, wherein the expanded volume portion comprises at least one thrombogenic material.

30. The medical device of claim 29, wherein the thrombogenic material comprises filaments and the filaments are substantially aligned with the longitudinal axis in the contracted state.

31. A medical device comprising:
   at least one layer of fabric defining a proximal end, a distal end, and an expanded volume portion between the proximal and distal ends, wherein the expanded volume portion defines a longitudinal axis extending between the proximal and distal ends;
   a first end feature attached to the proximal end of the at least one layer, wherein the first end feature defines opposing ends and further defines a first axis extending between the opposing ends, and wherein one of the opposing ends is positioned proximate the proximal end of the at least one layer; and
   a second end feature disposed at the distal end of the at least one layer, wherein the second end feature defines opposing ends and further defines a second axis extending between the opposing ends, and wherein one of the opposing ends is positioned proximate the distal end of the at least one layer,
   wherein the at least one layer is configured to self-expand from a contracted state when constrained within a delivery catheter toward an expanded state when deployed from the delivery catheter for delivery to a target site within the body lumen, and
   wherein at least one of the first end feature or the second end feature is angularly biased with respect to the expanded volume portion, such that, in the expanded state, a respective one of the first axis or the second axis is different from the longitudinal axis of the at least one layer and defines a preset angle with the longitudinal axis.

32. The medical device of claim 31, wherein the at least one layer of fabric comprises at least one metal selected from the group consisting of steel, stainless steel, shape memory alloy, and elastic alloy.

33. The medical device of claim 31, wherein the at least one layer of fabric comprises a polymer.

34. The medical device of claim 31, wherein the at least one layer of fabric comprises a first layer and a second layer, wherein the second layer is disposed within, adjacent to, or surrounding the first layer.

35. The medical device of claim 34, wherein the second layer comprises an elastomeric coating disposed adjacent the first layer.

36. The medical device of claim 34, wherein the relationship between the reduction in diameter and the elongation of the inner layer is substantially the same as the relationship between the reduction in diameter and the elongation of the outer layer as the medical device is moved between the expanded state and the contracted state.

37. The medical device of claim 31, wherein the expanded volume portion defines a recess configured to at least partially receive the first end feature or the second end feature.

38. The medical device of claim 31, wherein, in the expanded state, each of the first axis and the second axis is different from the longitudinal axis and defines a preset angle with the longitudinal axis that is between approximately 70°20 and approximately 120°.

* * * * *

UNITED STATES PATENT AND TRADEMARK OFFICE
CERTIFICATE OF CORRECTION

PATENT NO.        : 9,113,890 B2
APPLICATION NO.   : 13/367011
DATED             : August 25, 2015
INVENTOR(S)       : Anup Dasnurkar et al.

Page 1 of 1

It is certified that error appears in the above-identified patent and that said Letters Patent is hereby corrected as shown below:

In the specification

In Column 10, Line 57, delete "120, 1to" and insert therefor -- 120, to --.

In Column 13, Line 66, insert -- ) -- after "60°".

In the claims

In Claim 15, Column 18, Line 7, delete "7020" and insert therefor -- 70° --.

In Claim 22, Column 18, Line 67, delete "7020" and insert therefor -- 70° --.

In Claim 38, Column 20, Line 46, delete "7020" and insert therefor -- 70° --.

Signed and Sealed this
Eighth Day of March, 2016

Michelle K. Lee
*Director of the United States Patent and Trademark Office*